AZALEA PLANT
Filed Oct. 25, 1974
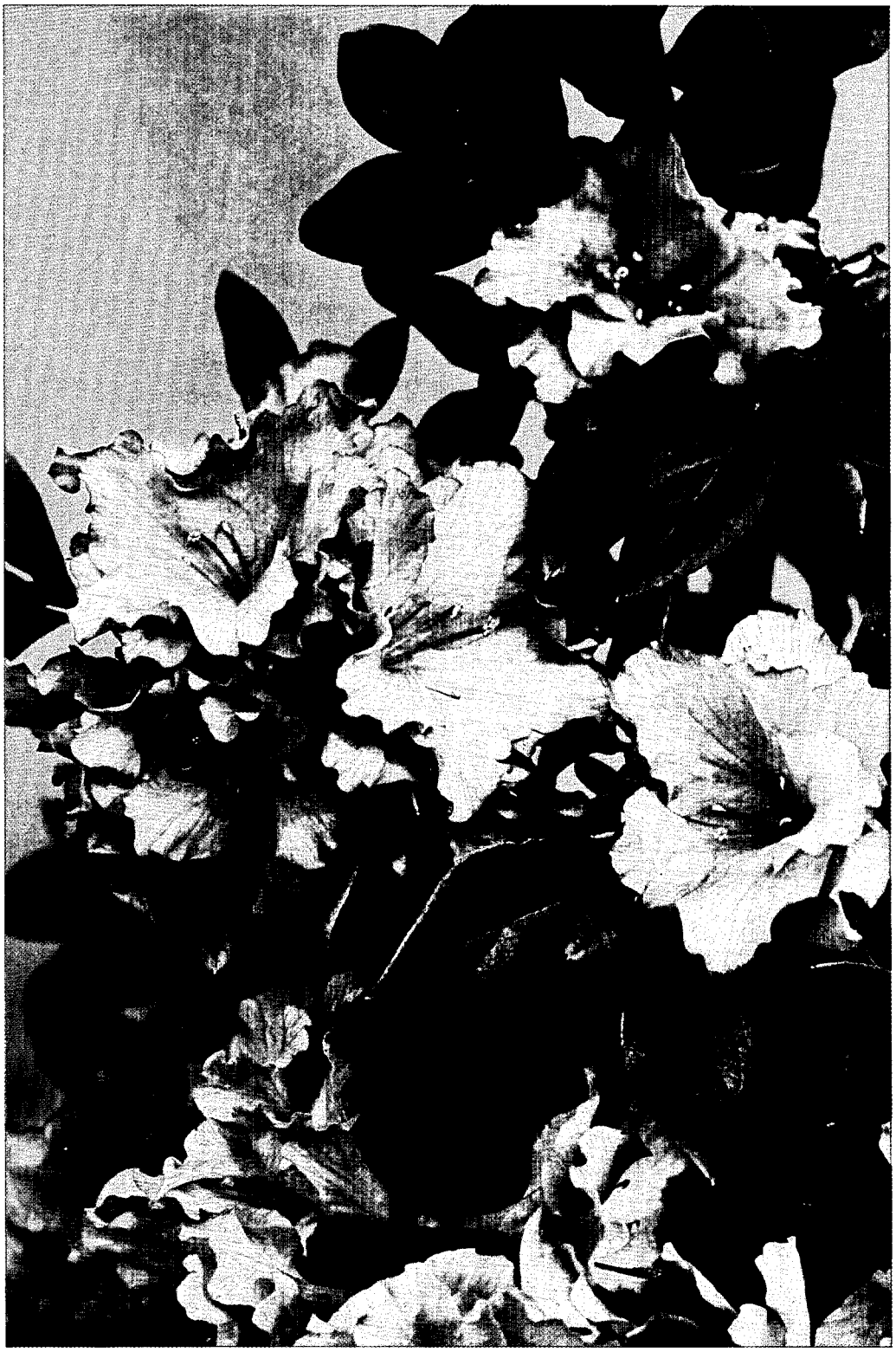

United States Patent

Plant Pat. 3,881
Patented May 11, 1976

3,881
AZALEA PLANT

James W. Hines, Jr., Corona Del Mar, Calif., assignor to Hines Wholesale Nurseries, Santa Ana, Calif.

Filed Nov. 25, 1974, Ser. No. 526,616
Int. Cl. A01h *5/00*
U.S. Cl. Plt.—57 1 Claim The present invention relates to a new and distinct variety of azalea plant. This plant was originated by me in March 1957, by crossing the azalea variety of the Southern Indica strain, Azalea "Twilight" (unpatented) with the azalea variety of the Belgian Indicia strain, Azalea "Twilight"/Azalea "Wm. Van Orange" (unpatented). The seeds which were produced by this hybridization were first sown in September 1957, and the plant first bloomed in March 1958.

As a result of this breeding, I have produced a new and improved azalea variety which is endowed with the following unique combination of characteristics which are outstanding therein, and which distingush the same from its parents, as well as from all other varieties of which I am aware.

The plant is characterized as to novelty by its ability to grow and flower in full sun or light shade in the southern California area without tip burning of the leaves or blasting of the flowers; by its abundant and rich green foliage and compact and dense habit of growth; by the unique coloring of its flowers; and by its profuse flowering.

The new variety has been asexually reproduced by me on my cultivated property on the Irvine Ranch, near Santa Ana, Calif. Several hundred cuttings of this new and distinct variety have been made since March 1963, and it holds its distinguishing characteristics through succeding propagations.

The drawings which accompany this petition show a typical view of the flowers and foliage of my new azalea variety. These are portrayed in color as fairly as can possibly be obtained by this method of illustration.

To facilitate identification of the important colors, I have used the color terminology of the R.H.S. Colour Chart issued by the Royal Horticultural Society of London.

Locality where grown and observed: On the Irvine Ranch, approximately 5 miles south of Santa Ana, Calif.

Parentage: Seedling resulting from planned propagation.

*Seed parent.*—Azalea "Twilight" an unpatented variety of the Southern Indica strain.

*Pollen parent.*—Azalea "Twilight"/Azalea "Wm. Van Orange," an unpatented variety of the Belgian Indica strain.

THE PLANT

Growth. The plant is of very vigorous growth habit, with dense branching, starting just above ground level. Flowering is prolific, with first blooms in late November, and heaviest bloom from late February into March. The plant is suitable for forcing. The plant has a stronger growth habit than the Belgian Indica variety, with plants in the nursery growing to a height of three feet.

Branches: New growth is in the Greyed-Orange Group, Plates 165B to 165C. Older branches are in the Greyed-Orange Group, Plates 166B to 166C. All branches are hirsute.

Foliage: The leaves are of good substance, semi-glossy and abundant.

Shape: Elliptic with an acute tip. Leaf margins are entire and slightly hairy.

Color:

*New leaves.*—Upper surface is in the Yellow-Green Group, Plates 144A to 144B. Underside is in the Yellow-Green Group, Plates 144B to 144C.

*Mature leaves.*—Upper surface is in the Green Group, Plates 137A to 137B. Underside is in the Yellow-Green Group, Plates 144A to 144B.

Size: New leaves range from ⅝ to ¾ inches in width, and 1½ to 1¾ inches in length. Mature leaves range from ⅞ to 1 inch in width, and 2 to 2⅛ inches in length.

Veins: Prominent and lighter in color than leaf, running from the petiole to the tip, and having pinnate veins extending therefrom.

THE FLOWER

The plant first flowers in late November, with heaviest bloom in late February, extending to mid-March, with occasional blooming thereafter. The flowers are borne 2 to 6 to a stem, regularly clustered, with flowers appearing both at the tips of the branches and slightly less in quantity toward mid-branch, creating a very floriferous effect.

Form: Flowers are ruffled, hose-in-hose.

Petals: 5 upper petals and 5 lower petals, and at maturity, blossoms range in size from 2½ to 2¾ inches in width, to a depth of 1¾ to 1⅞ inches.

Color: The color of the flowers ranges between the Red Group and the Orange-Red Group, having fluorescent-like sheen. The color tones range from a tone between Plate 33A and Plate 34A and a tone between Plate 53B and Plate 53C. Blotches are generally indistinct, with occasional evidence of faint blotching on the standard and upper wing corolla lobes only slightly darker in tone than the general flower color.

Buds: Long, tapered, and in the Red Group, shading from Plates 52B to 52C.

Reproductive organs: 6 to 10 stamens with the color in the Red Group, Plates 52A to 52B. They range from 1¼ to 1½ inches in length. Pollen—Yellow Group. Plates 4B to 4C.

I claim:

1. A new and distinct variety of azalea plant which is a hybrid of the Belgian Indica strain and the Southern Indica strain, and characterized in particular to novelty by its medium to abundant and rich green foliage and compact and dense habit of growth; by the unique fluorescent-like coloring of its flowers; and by its profuse flowering; and by its greater salts tolerance, making it less subject to root diseases common to other varieties grown in the same general area of the Irvine Ranch in southern California.

No references cited.

ROBERT E. BAGWILL, Primary Examiner